United States Patent [19]

McIntosh

[11] Patent Number: 4,647,601
[45] Date of Patent: Mar. 3, 1987

[54] SELF-SANITIZING EPOXY RESINS AND PREPARATION THEREOF

[75] Inventor: Robert H. McIntosh, Greensboro, N.C.

[73] Assignee: Interface Research Corporation, Atlanta, Ga.

[21] Appl. No.: 736,652

[22] Filed: May 21, 1985

Related U.S. Application Data

[63] Continuation-in-part of Ser. No. 570,952, Mar. 8, 1984, abandoned, which is a continuation of Ser. No. 523,734, Aug. 16, 1983, abandoned, which is a continuation of Ser. No. 226,006, Jan. 19, 1981, abandoned, which is a continuation of Ser. No. 149,555, May 13, 1980, abandoned, which is a continuation of Ser. No. 930,879, Aug. 4, 1978, abandoned.

[51] Int. Cl.$^4$ ............................................. C08K 5/52
[52] U.S. Cl. ................................... 523/122; 523/451
[58] Field of Search ................ 523/122, 451; 524/140; 514/76, 143

[56] References Cited

U.S. PATENT DOCUMENTS

| | | | |
|---|---|---|---|
| 2,541,088 | 2/1951 | Nikawitz | 260/584 |
| 2,676,122 | 4/1954 | McCarthy | 117/139.5 |
| 2,891,878 | 6/1959 | Chamberlain | 117/138.8 |
| 2,970,081 | 1/1961 | McCall | 167/30 |
| 3,247,134 | 4/1966 | Hwa | 260/2.5 |
| 3,279,986 | 10/1966 | Hyman | 167/42 |
| 3,280,131 | 10/1966 | Wakeman et al. | 260/286 |
| 3,308,488 | 5/1967 | Shooman | 5/335 |
| 3,364,192 | 1/1968 | Leach | 260/94.9 |
| 3,705,235 | 12/1972 | McIntosh | 424/83 |
| 3,762,415 | 8/1973 | Morrison | 128/287 |
| 3,896,101 | 7/1975 | McIntosh | 260/93.7 |
| 3,919,410 | 11/1975 | McIntosh | 424/78 |
| 3,920,836 | 11/1975 | McIntosh | 424/315 |
| 3,928,563 | 12/1975 | McIntosh | 424/78 |
| 3,959,556 | 5/1976 | Morrison | 428/364 |
| 3,979,307 | 9/1976 | Kolaian et al. | 514/76 |
| 4,024,324 | 5/1977 | Sparks | 524/141 |
| 4,110,504 | 8/1978 | Hull | 428/97 |
| 4,119,724 | 10/1948 | Thizy | 424/45 |
| 4,259,078 | 3/1981 | Kleber | 8/115.6 |
| 4,343,853 | 8/1982 | Morrison | 428/233 |
| 4,401,712 | 8/1983 | Morrison | 428/289 |
| 4,442,095 | 4/1984 | Johnston | 424/248.5 |
| 4,442,096 | 4/1984 | Johnston | 424/248.5 |

FOREIGN PATENT DOCUMENTS

| | | |
|---|---|---|
| 1162356 | 2/1984 | Canada . |
| 0035375 | 2/1981 | European Pat. Off. . |
| 2530584 | 7/1975 | Fed. Rep. of Germany . |
| 3014765 | 10/1981 | Fed. Rep. of Germany . |
| 3039437 | 5/1982 | Fed. Rep. of Germany . |
| 617854 | 12/1978 | Switzerland . |
| 1036578 | 8/1963 | United Kingdom . |

OTHER PUBLICATIONS

Carpet and Rug Industry, Feb. 1984 pp. 8–14 "Antimicrobials: Here to Stay . . .".
Carpet and Rug Industry, Apr., 1984, pp. 22–27 "Antimicrobial Activity on Carpet".
Abstract No. 1580026 (source unknown).
"Microbiology of Cooling Water", James W. McCoy, 1980 Chemical Publishing Co., NY, NY, pp. 94–95.

Primary Examiner—Veronica P. Hoke
Attorney, Agent, or Firm—Jones & Askew

[57] ABSTRACT

The present invention relates to self-sanitizing epoxy resin and to an additive which is incorporated therein so that the epoxy product or film is made self-sanitizing.

The additive is an alkyl phosphate derivative with the following structure:

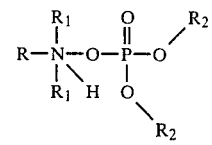

where R is an alkyl group of from 8 to 18 carbon atoms, $R_1$ is an alkyl group or a hydroxy alkyl group, and $R_2$ is selected from the group consisting of hydrogen and an alkyl group of from 6 to 18 carbon atoms, with at least one $R_2$ group being the alkyl group.

The additive is highly effective against both gram-negative and gram-positive bacteria and is also highly effective against eukaryotic microorganisms such as yeasts, molds and fungi. In addition to the unique and unexpected microbiocidal properties of the self-sanitizing epoxy, the microbiocidal activity remains in the epoxy product or film over long periods of time.

8 Claims, No Drawings

SELF-SANITIZING EPOXY RESINS AND PREPARATION THEREOF

RELATED CASES

This is a continuation-in-part patent application of Ser. No. 570,952 filed Mar. 8, 1984, now abandoned, which was a continuation of application Ser. No. 523,734 filed Aug. 16, 1983, now abandoned, which was a continuation of application Ser. No. 226,006 filed Jan. 19, 1981, now abandoned, which was a continuation of application Ser. No. 149,555 filed May 13, 1980, now abandoned, which was a continuation of application Ser. No. 930,879 filed Aug. 4, 1978, now abandoned.

TECHNICAL FIELD

The present invention relates to self-sanitizing epoxy resins and to an additive which is incorporated therein so that the epoxy product is made self-sanitizing. More particularly, the present invention concerns an epoxy substance and an additive for use therein, the combination of which may be applied in liquid form to surfaces or may be molded to form an object; the self-sanitizing epoxy destroying or significantly reducing dangerous or destructive microorganisms which may come in contact with the epoxy surface or the epoxy object.

BACKGROUND OF THE INVENTION

As used herein, the terms "antimicrobial", "bactericidal", and "fungicidal" describes the killing of, as well as the inhibition of or control of the growth of bacteria and fungi.

Epoxy resins, as used herein, are thermosetting resins based on the reactivity of the epoxide group. One type is made from epichlorhydrin and bisphenol-A. Molecules of this type have glycidyl ether structures in the terminal positions, have many hydroxyl groups and cure readily with amines. Other suitable epoxy resins include glycidated novolacs, epoxylated novolacs, and cycloaliphatic epoxy resins. The reactive epoxies form a tight cross-linked polymer network, and are characterized by toughness, good adhesion, corrosion and chemical resistance, and also have good dielectric properties.

Bacteria, fungi and other microorganisms are always present in our environment. The species and numbers of microorganisms vary depending on the general environment, on the nutrients and moisture available for the growth of the microorganisms, and on humidity and temperature of the local environment. Nutrients for these microorganisms abound in the normal environment. Any protein matter such as dried skin, discarded foods, plants and animal droppings all are excellent nutrient media for many types of potentially harmful microorganisms. In addition certain bacteria are capable of remaining viable in a dormant state on floors or on objects for long periods of time until they are deposited in the proper media for growth. These potentially harmful microorganisms can be transported merely by walking on floors, brushing against walls or by handling objects.

The floors and walls found in buildings such as hospitals are particularly susceptible to contamination by bacteria and other harmful organisms. In fact, the floors and walls of hospitals are a major source of nosocomial (hospital-acquired) infections. Conventionally, these surfaces are periodically cleaned with cleansers to remove accumulated microorganisms. Between these cleanings, however, it is quite possible that the surfaces may accumulate a sufficient quantity or quality of bacteria or other microorganisms to constitute a major source of cross-infection or spread of disease.

Microorganisms contamination on walls and floors is also a major problem in industry. For example, the floors of breweries must often be repainted due to the constant yeast contamination from the fermentation process. The organisms apparently reside either on the surface of the floor under the paint or in the floor substrate (such as in concrete) under the paint and cause conventional floor coverings such as epoxy, to detach after a short period of time. The problem of microorganism contamination from walls and floors is particularly serious in industries which manufacture health related products such as drugs or biodiagnostic chemicals. Tremendous resources are expended in an attempt to reduce microorganism contamination in these industries.

Another major source of microbial contamination is from the handling of everyday objects. Bacteria and other microorganisms that are present in the environment will often be deposited on an object that is handled by several people. When one person puts the object down and another person picks it up, the microorganism can easily be transferred from the first person to the object and then to the second person. This is an especially harmful problem in hospitals where medical personnel routinely travel from one patient to another and can inadvertently transfer an especially serious microorganism to an object such as a medical chart, a pencil or any other object. A second medical personnel will then touch the object (called a fomite) and transfer the microorganism to their body. If the second medical personnel then examines or treats a second patient, the microorganism may be transferred to that patient and cause a serious secondary infection in the patient or even in the medical personnel.

A major problem encountered in the control of microorganisms is the extreme variability of response of the various microorganisms to conventional sanitizing agents. For example, bacteria, which are classified as prokaryotes, can be killed or inhibited by many different types of antibiotics. These same antibiotics that are highly effective against the prokaryotic organisms are usually highly ineffective against the eukaryotic microorganisms such as fungi and yeasts. Even within the family of Bacterioaceae, there are two broad categories of bacteria known as gram-positive and gram-negative bacteria. The classifications stem from the ability or non-ability of bacteria to absorb certain vital stains. The two groups of bacteria generally respond quite differently to the same microbiocidal agent. A particular agent that may be highly effective against one group, very likely may not be effective against the other group.

One conventional method of inhibiting the growth of both eukaryotes and prokaryotes and gram-negative and gram-positive bacteria is to combine two or more microbiocidal inhibitors; each designed to inhibit or kill a specific organism or class of organisms. However, various problems arise when introducing two or more additives into a material such as epoxy resin. The multiple additive system may alter the physical properties of the epoxy resin into which it is added. In addition, the multiple components must be tested to ensure their compatibility and continued microbiocidal effectiveness when combined with the material to be sanitized. The relative microbiocidal or microbiostatic strength of each of the components in the multiple system must be determined. It is not uncommon to produce an epoxy resin which may initially have effective inhibiting properties for both gram-positive and gram-negative organisms whereupon, with the passage of time, one or the other of the inhibiting additives will deteriorate and greatly lose its effectiveness while the other inhibiting additive remains effective. One additive may have an unexpected inhibitory effect on the other additive. In addition, the requirement of adding two or more additives can become prohibitively expensive.

SUMMARY OF THE INVENTION

The present invention solves the above problems by providing a self-sanitizing epoxy resin, including a homogeneously distributed additive therein and a method of preparation thereof, which is effective in killing or significantly inhibiting the growth of a wide spectrum of both prokaryotic and eukaryotic microorganisms which may come into contact with surfaces covered with the self-sanitizing epoxy or with objects made of the self-sanitizing epoxy that comprises the present invention.

In accordance with the present invention, it has been determined that certain alkyl phosphate derivatives can be dispersed into a liquid epoxy resin to provide unique and unexpected fungicidal and bactericidal properties to the epoxy resin. The unique and unexpected sanitizing properties of the alkyl phosphate derivatives remain even after the epoxy resins have hardened to form the final product. In addition, the unique and unexpected microbiocidal properties of the alkyl phosphate derivative remain for long periods of time after dispersion in the epoxy resin and subsequent hardening.

The self-sanitizing epoxy resin of this invention has the capacity to kill or inhibit the growth of many types of bacteria, fungi, yeasts and other destructive or disease-producing microorganisms which might come into contact with a surface covered with the self-sanitizing epoxy of the present invention or with an object made of the self-sanitizing epoxy. In addition, the self-sanitizing epoxy resin of the present invention may be formulated to be particularly effective against both gram-positive bacteria, such as *Staphylococcus aureus*, and gram-negative bacteria, such as *Pseudomonas aeruginosa* and *Pseudomonas cepacia*.

The present invention also comprises a method for the preparation of and the incorporation into epoxy resins of the alkyl phosphate derivatives that give the epoxy resin the ability to kill or significantly reduce bacterial growth, fungal growth and yeast growth in and on the epoxy coating or epoxy object over a long period of time. In addition and unexpectedly, by adjusting the concentration of the reactants in the preparation of the alkyl phosphate derivative of the present invention, the bactericidal activity of the resulting alkyl phosphate derivative can be selected. The alkyl phosphate derivative can be prepared so that it is effective primarily against gram-negative bacteria, against gram-positive bacteria or both.

The epoxy resin with the additive contained therein can be used as a protective coating such as a paint, or the epoxy can be formulated with an aggregate to form, in itself, a heavy duty flooring system that has self-sanitizing qualities that will remain for long periods of time. In addition the epoxy resin with the additive contained therein can be used to form molded objects thereby rendering the object self-sanitizing.

It is therefore an objective of the present invention to provide a chemical compound which can be incorporated into epoxy resins which provide microbiocidal activity against both gram-positive and gram-negative organisms include *Pseudomonas aeruginosa* and *Pseudomonas cepacia*.

It is another objective of the present invention to provide a chemical compound which can be incorporated into epoxy resins and which provides effective microbiocidal activity against a wide variety of bacteria, yeasts, molds and fungi.

It is another objective of the present invention to provide an effective microorganism inhibiting agent which is relatively inexpensive and which requires no special handling procedures or techniques.

It is another objective of the present invention to provide a sanitizing agent wherein the compound is highly effective in killing or inhibiting the growth of microbial organisms but is safe for use around humans and animals.

It is yet another objective of the present invention to provide a sanitizing agent which is effective against both gram-positive and gram-negative organisms over a wide range of concentrations.

It is another objective of the present invention to provide a sanitizing agent wherein the selectivity can be varied so as to inhibit either gram-negative or gram-positive bacteria or inhibit both types of bacteria.

It is yet another objective of the present invention to provide a sanitizing agent which can be incorporated over a wide concentration range without adversely affecting the physical properties of the epoxy resin.

These and other objects, features and advantages of the present invention will become apparent after a review of the following detailed description of the preferred embodiment and the appended claims.

DETAILED DESCRIPTION OF THE PREFERRED EMBODIMENT

In accordance with the present invention, the epoxy resin contains an alkyl phosphate derivative sanitizing additive which is uniformly dispersed throughout the material. An unexpected aspect of the combination of epoxy resin and alkyl-phosphate derivatives is the unique ability of the additive to diffuse through the hardened epoxy material and continually replenish the additive that is removed from the surface of the epoxy film or the epoxy object through washing or wear.

It has been found that the active sanitizing additive diffuses to the surface of the epoxy film or object at a rate sufficient to maintain a level of concentration that will inhibit the growth of a wide spectrum of common bacteria, fungi and yeasts for long periods of time.

The antimicrobial activity of the compounds of the present invention has been confirmed using standard laboratory techniques. Growth of the following organisms, including both gram-negative and gram-positive bacteria, has been found to be inhibited by the present invention: *Sarcina lutea*, Staphylococcus species, *Pseudomonas aeruginosa*, *Pseudomonas cepacia*, *Escherichia coli*, Klebsiella species, *Candida albicans*, Salmonella species, *Enterobacter aerogenes*, Streptococcus species. These microorganisms are representative of those organisms that are responsible for major infections in hospitals and other health care facilities. In addition, these organisms are also involved in industrial contamination causing untold delays and destruction.

The sanitizing additive of the present invention is an alkyl phosphate derivative of the following formula:

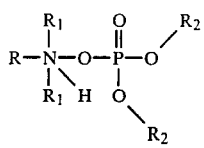

where
R = an alkyl group of from 8 to 18 carbon atoms;
$R_1$ = an alkyl group of from 1 to 18 carbon atoms or a hydroxy alkyl group;
$R_2$ = hydrogen or an alkyl group of from 6 to 18 carbon atoms with at least one of the $R_2$ groups being the alkyl group.

In a preferred form of this additive, $R_1$ is a hydroxy alkyl group of from 1 to 18 carbon atoms.

The microbiocidal additive of the present invention is comprised of the mono-ester form of the alkyl phosphate derivative, the di-ester form of the alkyl phosphate derivative or a mixture of mono-esters and di-esters with the general structure of the formula above. In the mono-ester, one $R_2$ group is an alkyl group of 6 to 18 carbon atoms and the other $R_2$ group is a hydrogen. In the di-ester, the two $R_2$ groups are alkyl groups of 6 to 18 carbon atoms.

In order to function as a broad spectrum bacteriostatic or bacteriocidal agent, a compound must inhibit both gram-positive and gram-negative bacteria. In addition, there are situations where one would desire to inhibit the growth of either the gram-positive or the gram-negative bacteria. It is a unique and unexpected finding of the present invention that by merely adjusting the ratio of di-ester to mono-ester, the effectiveness of the compound against either gram-positive or gram-negative bacteria or both, can be determined.

Thus, it has been determined that the inhibitory properties of the present invention depend upon the molar ratio of the following mono- and di-phosphoesters:

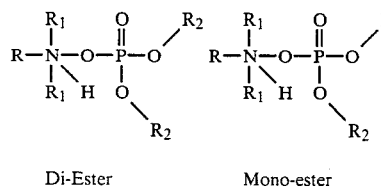

Di-Ester          Mono-ester where
R = an alkyl group of from 8 to 18 carbon atoms;
$R_1$ = a alkyl group of from 1 to 18 carbon atoms or a hydroxy alkyl group;
$R_2$ = an alkyl group of from 6 to 18 carbon atoms.

The molar ratio of the reactants required to synthesize the microbiocidal additive determines the ratio of the mono- and di-phosphoesters of the final phospho alkyl derivative. By adjusting the concentrations of the reactants in the synthesis, a mixture of mono- and di-phospho alkyl esters can be selected that will be effective in killing or inhibiting a particular group or groups of microorganisms.

The following examples will serve to further illustrate the present invention without, at the same time, however, constituting any limitation thereof.

EXAMPLE I

The preparation of the alkyl phosphate derivatives of the present invention involves two reactions. In the first reaction, one mole of phosphorous pentoxide is reacted with three moles of 2-ethylhexanol in the following manner. The 2-ethylhexanol is heated to a temperature of between approximately 80° C. and 120° C. The preferred temperature for the reaction is 100° C. The phosphorous pentoxide is slowly added to the 2-ethylhexanol while the mixture is vigorously agitated. At the preferred reaction temperature of 100° C., the reaction is complete in about two hours. The progress of the reaction can be determined by titrating the acid that is produced with a solution of potassium hydroxide. For the above disclosed ratio of reactants, the reaction is complete when 316.6 equivalents of base are neutralized.

The product formed in this reaction is a mixture of 2-ethylhexyl acid phosphate and di(2-ethylhexyl) acid phosphate. The reaction equation is as follows:

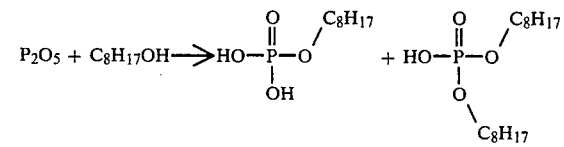

In the second reaction, the mixed phosphodiester is then reacted with bis(hydroxyethyl) cocoamine as shown in the following reaction.

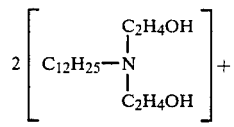

bis(hydroxyethyl) cocoamine

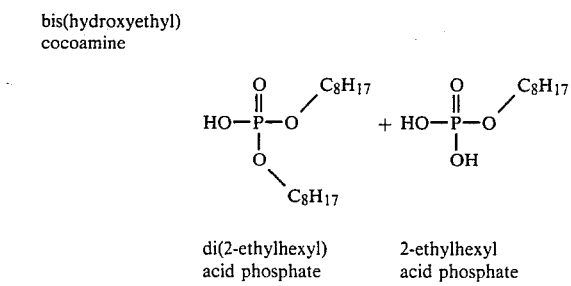

di(2-ethylhexyl) acid phosphate      2-ethylhexyl acid phosphate

Resulting in a mixture of the following mono- and di-ester products

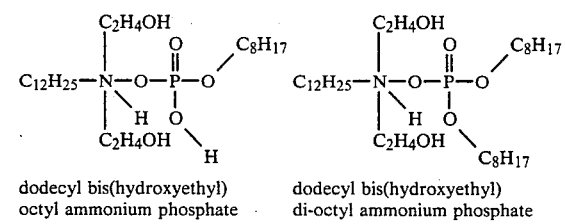

dodecyl bis(hydroxyethyl) octyl ammonium phosphate      dodecyl bis(hydroxyethyl) di-octyl ammonium phosphate To obtain the preferred microbiocidal additive of the present invention, the second reaction is carried out in the following manner. Approximately 1.3 moles of bis(hydroxyethyl) cocoamine per mole of mixed diphospho-2-ethylhexyl esters is slowly added to the mixture from the first reaction until the pH is between approximately 3.2 and 3.8 in a 75% ethanol solution. This reaction is carried out at a preferred temperature of 100° C. although the reaction can be performed at temperatures between approximately 80° C. and 120° C. The reaction mixture is vigorously agitated during the reaction. The resulting reaction product is approximately 66% by weight of the bis(hydroxyethyl) di-octyl ammonium phosphate and approximately 16% by weight of the bis(hydroxyethyl) octyl ammonium phosphate. The remaining 18% of the solution is made up of inert components. The alkyl phosphate microbiocidal additive of reaction 2 is added directly to the epoxy resin at a concentration of between 0.1 and 15% by weight with a preferred concentration of between approximately 1% and 10%.

EXAMPLE II

One of the important and unexpected properties of the present invention is the ability to select the mcirobiocidal activity of the alkyl phosphate derivative by varying the ratio of the reactants in Example I. It has been found that by adjusting the molar ratio of bis(hydroxyethyl) cocoamine to the 2-ethylhexyl acid phosphate mixed esters in the reaction described in Example I, one can select the microbiocidal activity of the sanitizing agent of the present invention between gram-negative and gram-positive bacteria. For example, in some cases, it may be desirable to have optimum inhibition or killing against both gram-negative and the gram-positive bacteria or, in other cases, one may be interested only in inhibiting or killing either gram-positive or gram-negative bacteria.

The microbiocidal activity of the sanitizing agent of the present invention is evaluated as follows. Petri dishes are prepared using appropriate nutrient agar as a food source for the microorganisms; each microorganism is evenly streaked onto the agar to form a lawn of microorganism as is well known to one skilled in the art. A *Staphylococcus aureus* is used as a bacteria representative of the gram-positive bacteria and a *Pseudomonas aeruginosa* is used as a bacteria representative of the gram-negative bacteria. 0.05 mls. of each of the indicated test compounds was placed in the center of an innoculated petri dish and incubated for 24 hours at 37° C. After the 24 hour incubation period, the relative susceptibility of the test organism to the sanitizing agent of the present invention is demonstrated by a clear zone of growth inhibition around the test solution. This is the result of two processes: (1) the diffusion of the compound and (2) growth of the bacteria. As the antimicrobial compound diffuses through the agar medium from the edge of the drop, its concentration progressively diminishes to a point where it is no longer inhibitory for the test organism. The size of this area of suppressed microbial growth, the zone of inhibition, is determined by the concentration of antimicrobic present in the area. Therefore, within the limitations of the test, the area of the inhibition zone is proprotional to the relative susceptibility of the microorganisms to the sanitizing compound of the present invention.

After the 24 hour incubation period, each plate is examined and the diameters of the complete inhibition zones are noted and measured using either reflected light and sliding calipers, a ruler, or a template prepared for this purpose and held on the bottom of the plate. The end point, measured to the nearest millimeter, should be taken as the area showing no visible growth that can be detected with the unaided eye.

In this example, varying ratios of the two reactants, bis(hydroxyethyl) cocoamine and the mixed mono- and di-ester phosphated 2-ethylhexanol from the reaction in Example I, are reacted together as described in Example II. The reactants used in this example are as follows:
1 = Bis(hydroxyethyl) cocoamine
2 = Phosphated 2-ethylhexanol (mixed mono- and di-ester) from the first reaction described in Example I.

These components are reacted in the following ratios under the conditions described in Example I. The product of that reaction is then tested for microbiocidal activity against the gram-positive *Staphylococcus aureus* and the gram-negative *Pseudomonas aeruginosa*.

The results are summarized in Table I.

TABLE I

| Molar Ratio Of Reactants | S. aureas Area Of Inhibition Measured In mm | P. aeruginosa |
|---|---|---|
| A. (2) only | 35 | 15 |
| B. 0.5 Mole (1)/1 Mole (2) | 22 | 14 |
| C. 1.0 Mole (1)/1 Mole (2) | 17 | 15 |
| D. 1.3 Mole (1)/1 Mole (2) | 12 | 20 |
| E. 1.5 Mole (1)/1 Mole (2) | 12 | 3 |
| F. 2.0 Mole (1)/1 Mole (2) | 12 | 2 |
| G. 2.5 Mole (1)/1 Mole (2) | 8 | 2 |
| H. 3.0 Mole (1)/1 Mole (2) | 7 | 0 |
| I. (1) only | 7 | 0 |

The preferred ratio of reactants for a reaction product that exhibits approximately the same inhibition of the gram-positive and gram-negative bacteria is approximately 0.5 to 1.3 moles bis(hydroxyethyl) cocoamine reacting with one mole phosphated 2-ethylhexanol mixed ester from the reaction described in Example I. This reaction is not limited to these specific reactants, since alcohols, both normal and isomeric, and amines of various classes and molecular weight would behave in a similar manner.

EXAMPLE III

An epoxy paint system using the sanitizing additive of the present invention is formulated as follows:
Epoxy resin: 88.2% by weight;
TlO₂: 9.8% by weight;
Product from 2.0% by weight. Example I:

The epoxy resin used in this example is referred to as DGEBPA or diglycidyl ether of bisphenol-A (Dow Chemical Company, Midland, Mich.). Epoxy resins that can be used with the present invention are epichlorohydrin/bisphenol-A, glycidated novolacs, epoxylated novolacs, and cycloaliphatic epoxy resins.

It has been determined that a ratio of the di-ester (dodecyl bis(hydroxyethyl) di-octyl ammonium phosphate) to the mono-ester (dodecyl bis(hydroxyethyl) octyl ammonium phosphate) of between approximately 1:1 and 6:1 is effective against a wide variety of microorganisms with a preferred ratio of di-ester to mono-ester of between approximately 3.8:1 and 4.4:1.

The alkyl phosphate derivative used in this example is the product of Example I. This additive is the one most effective against both gram-positive and gram-negative bacteria. The concentration of the additive in this particular example is approximately 2% which gives a final concentration of each of the components of the microbiocidal additive as follows:

1.33% dodecyl bis(hydroxyethyl) di-octyl ammonium phosphate 0.32% dodecyl bis(hydroxyethyl) octyl ammonium phosphate.

The ratio of di-ester to mono-ester in this particular example is approximately 4.1:1.

Although the alkyl phosphate additive is used at a concentration of 2.0% in this particular example, the sanitizing agent of the present invention has been found to be effective in killing or inhibiting the growth of microorganisms at a concentration of between approximately 0.1% and 15% by weight with a preferred range of between approximately 1% and 10%.

After thoroughly mixing the above ingredients the resin system is allowed to react with a stoichiometric amount of hardener (cross linking reagent). Before the cross-linking reaction is completed, samples of the self-sanitizing epoxy are poured into 100×15 mm. test tubes. Upon completion of the reaction, the epoxy sample is hard and measures 60×2×15 mm. and weighs approximately 28.89 grams. Samples are cut in the form of discs (surface area of 176.83 mm² per side) and placed in petri dishes containing a nutrient agar (Trypticase Soy Nutrient Agar, Baltimore Biological Laboratory, Cockeysville, Md.) inoculated with a lawn of the indicated microorganism. It is found, upon incubation of the dishes, that the epoxy disc inhibits the growth of bacteria and fungi around the specimen and creates a zone of inhibition. The results of the test are as follows:

TABLE II

| Organisms | Type Of Organism | Area of Inhibition In mm |
| --- | --- | --- |
| S. aureus | gram-pos. bacteria | 10 |
| P. aeruginosa | gram-neg. bacteria | 3 |
| E. coli | gram-neg. bacteria | 11 |
| K. species | gram-neg. bacteria | 11 |
| C. albicans | yeast | 7 |
| S. choleraesuis | gram-neg. bacteria | 12 |
| A. niger | fungus | 3 |
| T. mentagrophyte | fungus | 4 |
| B. megaterium | gram-pos. bacteria | 2 |

The sanitizing agent of the present invention can be added to epoxy based paints to reduce the formation of mold and other such organisms on painted surfaces. In addition, the sanitizing agent of the present invention may be added to an epoxy resin that is to be molded into objects, thereby imparting long-term microbiocidal activity to the object.

While this invention has been described in detail with particular reference to preferred embodiments thereof, it will be understood that variations and modifications can be effected within the spirit and scope of the invention as described hereinbefore and as defined in the appended claims.

I claim:

1. A self-sanitizing epoxy resin including a homogeneously distributed alkyl phosphate derivative therein, said alkyl phosphate having the following formula:

$$\begin{array}{c} R_1 \quad\ O \quad\ R_2 \\ | \quad\ \| \quad / \\ R-N-O-P-O \\ | \ \backslash \quad | \\ R_1 \ H \quad O \\ \quad\quad\quad\ \backslash \\ \quad\quad\quad\quad R_2 \end{array}$$

wherein R is an alkyl group of from 8 to 18 carbon atoms, $R_1$ is an alkyl group or a hydroxy alkyl group, and $R_2$ is a hydrogen or an alkyl group of from 6 to 18 carbon atoms with at least one of the $R_2$ groups being the alkyl group; and said alkyl phosphate derivative is present in the epoxy resin at a concentration between approximately 0.1% and 15% by weight.

2. The self-sanitizing epoxy resin of claim 1, wherein said alkyl phosphate derivative is present in said epoxy resin at a concentration between approximately 1% and 10% by weight.

3. The self-sanitizing epoxy resin of claim 1, wherein said $R_1$ group of said alkyl phosphate derivative is a hydroxy alkyl group.

4. The self-sanitizing epoxy resin of claim 1, wherein said $R_2$ group of said alkyl phosphate derivative is an alkyl group of 8 carbon atoms.

5. The self-sanitizing epoxy resin of claim 1 wherein the alkyl phosphate derivative is dodecyl bis(hydroxyethyl) octyl ammonium phosphate.

6. The self-sanitizing epoxy resin of claim 5 wherein the alkyl phosphate derivative is present at a concentration of approximately 2%.

7. The self-sanitizing epoxy resin of claim 1, wherein said epoxy resin is selected from the group consisting of epichlorohydrin/bisphenol-A, glycidated novolacs, epoxylated novolacs and cycloaliphatic epoxy resins.

8. The self-sanitizing epoxy resin of claim 6, wherein said epoxy resin is selected from the group consisting of epichlorohydrin/bisphenol-A, glycidated novolacs, epoxylated novolacs and cycloaliphatic epoxy resins.

* * * * *